(12) United States Patent
Pugh

(10) Patent No.: US 6,847,451 B2
(45) Date of Patent: Jan. 25, 2005

(54) APPARATUSES AND METHODS FOR ANALYTE CONCENTRATION DETERMINATION

(75) Inventor: Jerry T. Pugh, Mountain View, CA (US)

(73) Assignee: LifeScan, Inc., Milpitas, CA (US)

(*) Notice: Subject to any disclaimer, the term of this patent is extended or adjusted under 35 U.S.C. 154(b) by 286 days.

(21) Appl. No.: 10/137,097

(22) Filed: May 1, 2002

(65) Prior Publication Data

US 2003/0206302 A1 Nov. 6, 2003

(51) Int. Cl.[7] .......................... G01N 21/00; G01N 21/29
(52) U.S. Cl. ........................ 356/436; 356/39; 422/82.05
(58) Field of Search .................. 356/436, 446, 356/39–42; 422/82.05; 435/808

(56) References Cited

U.S. PATENT DOCUMENTS

| | | | |
|---|---|---|---|
| 4,806,002 A | * | 2/1989 | Simeth et al. ............... 356/445 |
| 4,867,946 A | | 9/1989 | Gross et al. |
| 4,935,346 A | | 6/1990 | Phillips et al. |
| 4,957,363 A | | 9/1990 | Takeda et al. |
| 5,059,394 A | | 10/1991 | Phillips et al. |
| 5,114,350 A | * | 5/1992 | Hewett ......................... 422/58 |
| 5,137,364 A | | 8/1992 | McCarthy |
| 5,304,468 A | | 4/1994 | Phillips et al. |
| 5,335,659 A | * | 8/1994 | Pologe ........................ 600/328 |
| 5,408,535 A | | 4/1995 | Howard, III et al. |
| 5,429,129 A | * | 7/1995 | Lovejoy et al. ............. 600/323 |
| 5,889,585 A | | 3/1999 | Markart |
| 6,055,060 A | | 4/2000 | Bolduan et al. |
| 6,124,585 A | | 9/2000 | Riedel et al. |
| 6,249,593 B1 | | 6/2001 | Chu et al. |
| 6,294,133 B1 | | 9/2001 | Sawada et al. |
| 6,420,128 B1 | * | 7/2002 | Ouyang et al. ............... 435/25 |
| 6,707,554 B1 | * | 3/2004 | Miltner et al. ............... 356/436 |

FOREIGN PATENT DOCUMENTS

| | | |
|---|---|---|
| EP | 0087466 | 1/1988 |
| EP | 0646784 | 4/1995 |
| EP | 0819 943 A2 | 1/1998 |
| EP | 1130 382 A1 | 5/2001 |

OTHER PUBLICATIONS

Patent Application Publication US 2001/0031503 A1, published on Oct. 18, 2001, By Challener et al. Entitled Optical Assaying Method and System Having Movable Sensor With.

* cited by examiner

Primary Examiner—Zandra Smith
Assistant Examiner—Kara Geisel
(74) Attorney, Agent, or Firm—Susan C. Tall; Bozicevic, Field & Francis, LLP (57) ABSTRACT

Apparatuses and methods for determining the concentration of an analyte in a physiological sample are provided. The subject apparatuses include at least one light source, a detector array, means for determining whether a sufficient amount of sample is present on each of the plurality of different areas, and means for determining the concentration of the analyte based on the reflected light detected from those areas determined to have sufficient sample, where areas having insufficient sample are not used in analyte concentration determination. The subject methods include illuminating each area of a test strip, obtaining reflectance from each of the different areas, determining which areas have sufficient sample based on detected light therefrom and deriving analyte concentration from the areas determined to have sufficient sample, where areas determined not to have sufficient sample are not used in the derivation. Also provided are kits for use in practicing the subject methods.

22 Claims, 4 Drawing Sheets

APPARATUSES AND METHODS FOR ANALYTE CONCENTRATION DETERMINATION

FIELD OF THE INVENTION

The field of this invention is analyte concentration determination.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like.

In response to this growing importance of analyte concentration determination, a variety of analyte concentration determination protocols and devices for both clinical and home testing have been developed and, specifically, a variety of analyte measurement devices and methods for enabling patients to test their own blood for the presence and concentration determination of a variety of different analytes are well known in the art. Of great interest and use in this area are optical based measurement devices and methods in which a sample is illuminated and reflected light therefrom is detected to obtain an analyte concentration. Of increasing interest in such optical based measurement protocols is the use of assay systems that employ test strips or cards and meters for reading these test strips. Typically, a physiological sample such as blood, blood derivatives, interstitial fluid, urine, etc. is introduced to a test strip to wet a particular testing or measurement area of the test strip. The sample reacts with certain reagents or components associated with the testing area to produce a color change in those areas where the test strip has been wetted by the sample. Reflected light detected from this testing area is what is used to obtain an analyte concentration, as mentioned above, by relating the amount of reflected light to analyte concentration.

A characteristic of devices and methods that provide for analyte concentration determination using a measured reflectance value is that sample size and the uniform or even distribution thereof can have an impact on the final measurement, where a sample size that is too small or a sample that is not uniformly applied can cause erroneous or inaccurate results. Specifically, if an insufficient volume of sample is applied to the test strip and/or sample is not uniformly applied, only a portion of the testing area is wetted by the sample while other portions of the testing area are not wetted. In conventional optical based measurement devices and methods, light is detected from the entire testing area, including those portions that are not wetted by sample. However, the use of light detected from non-wetted portions of the testing area can cause the determination of analyte concentration to be erroneous or inaccurate.

Attempts at solving the above described problems of insufficient and/or non-uniformly applied sample have not been wholly adequate. In the simplest process, it is incumbent upon the user to visually monitor whether sufficient sample has been applied and whether the testing area has been uniformly wetted. However, such visual monitoring is not very reliable, especially for persons with diabetes who typically have impaired vision.

In another attempt to solve the problems described above, EPB0087466 describes an apparatus that estimates whether the amount of sample is sufficient on the basis of absorption of water in the infrared region of the electromagnetic spectrum. However, such an apparatus requires a means for quantitative analysis and an infrared transducer and receiver and is therefore disadvantageous for use as a portable system such as for home glucose testing by diabetics. Furthermore, in using the apparatus disclosed in EPB0087466, instances where sample is non-uniformly applied can not be easily identified.

U.S. Pat. Nos. 5,889,585 and 6,055,060 also attempt to solve the problem described above by comparing values obtained from two different test strip sites to each other, where a certain magnitude of deviation indicates that the measuring field is not uniformly wetted. When non-uniformity is indicated, the user is prompted to apply more sample or, in certain instances, prompted that too much time has elapsed and a new test must be commenced. That is, neither the '585 patent nor the '060 patent provides for analyte concentration determination using the small sample provided and/or the unevenly wetted measurement area and instead requires the user to apply more sample to the test strip or begin a new test. Neither of these options is wholly satisfactory.

In the instance where the user is prompted to apply more sample, the user either has to attempt to squeeze the initial site of the needle stick in order to try to "milk" or massage more blood out of that site or the user must pierce their skin once again at another site. Because blood clots quickly, by the time the user is prompted to apply more blood, it is not uncommon that another site must be pierced with a needle. The piercing procedure for obtaining sample can be painful, where it will be obvious that the pain is compounded when the skin needs be pierced multiple times in order to obtain the requisite sample volume to conduct the test. Due to this pain, it is not uncommon for individuals who require frequent monitoring of an analyte to simply avoid monitoring the analyte of interest all together. With diabetics, for example, the failure to measure their glucose level on a prescribed basis results in a lack of information necessary to properly control the level of glucose. Uncontrolled glucose levels can be very dangerous and even life threatening.

In the instance where a new, second test must be commenced, a new test strip is required for the second test. As such, the test strip used for the first, uncompleted test is discarded in place of a new test strip for use with the second test, resulting in the use of two test strips, rather than one, for a single analyte concentration determination. This increases the already high cost of test strip-based analyte concentration determination.

As such, there is continued interest in the development of new devices and methods for analyte concentration determination that provide accurate analyte concentrations in the cases where small sample volumes are applied to a test strip measurement area and/or the measurement area of the test strip is not evenly or uniformly wetted by sample. Of particular interest would be the development of such devices and methods which are easy to use, particularly for visually impaired individuals, involve minimal pain and are portable.

SUMMARY OF THE INVENTION

Apparatuses and methods for determining the concentration of an analyte in a physiological sample are provided. The subject apparatuses include at least one light source for irradiating a plurality of different areas of a test strip that has been inserted into the apparatus, a detector array for detecting reflected light from each of the plurality of different areas respectively, means for determining whether a sufficient amount of sample is present on each of the plurality of different areas by determining reflected light therefrom, and means for determining the concentration of the analyte based on the reflected light detected from those areas determined to have sufficient sample, where areas determined not to have sufficient sample are not used in the analyte concentration determination.

In the subject methods for determining the concentration of an analyte in a physiological sample applied to a test strip, a plurality of different areas of the test strip having physiological sample applied thereto are illuminated, a respective reflectance value is obtained from each of the plurality of different areas, the obtained reflectance data from each of the plurality different areas is determined to be indicative of a sufficient amount of sample or not, and the concentration of the analyte in the physiological sample is derived from the areas determined to have sufficient sample, where areas determined not to have sufficient sample are not used in the derivation. Also provided are kits for use in practicing the subject methods.

DETAILED DESCRIPTION OF THE INVENTION

Apparatuses and methods for determining the concentration of an analyte in a physiological sample are provided. The subject apparatuses include at least one light source for irradiating a plurality of different areas of a test strip that has been inserted into the apparatus, a detector array for detecting reflected light from each of the plurality of different areas respectively, means for determining whether a sufficient amount of sample is present on each of the plurality of different areas by determining reflected light therefrom, and means for determining the concentration of the analyte based on the reflected light detected from those areas determined to have sufficient sample, where areas determined not to have sufficient sample are not used in the analyte concentration determination.

In the subject methods for determining the concentration of an analyte in a physiological sample applied to a test strip, a plurality of different areas of the test strip having physiological sample applied thereto are illuminated, a respective reflectance value is obtained from each of the plurality of different areas, the obtained reflectance data from each of the plurality different areas is determined to be indicative of a sufficient amount of sample or not, and the concentration of the analyte in the physiological sample is derived from the areas determined to have sufficient sample, where areas determined not to have sufficient sample are not used in the derivation. Also provided are kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a reagent" includes a plurality of such reagents and reference to "the apparatus" includes reference to one or more apparatuses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject devices are described first. Next, a description of the subject methods is provided, followed by a review of kits which include the subject devices.

Devices

As mentioned above, the subject devices includes apparatuses for determining the concentration of at least one analyte in a physiological sample applied to a test strip that is inserted into a subject apparatus. More specifically, the apparatuses of the subject invention enable the determination of the concentration of at least one analyte in a physiological sample, even in those instances where the measurement area of the test strip is not uniformly wetted, for example because an insufficient amount of sample is applied thereto and/or because sample applied thereto is not evenly distributed over the entire measurement area. Generally, the subject apparatuses can be characterized as optically-based meters and are configured for receiving a test strip, such as the type of test strip described below. The optical apparatuses read the test strip or determine analyte concentration of a sample applied to the test strip by illuminating a plurality of different areas of the test strip and measuring detecting reflected light from each area separately using at least one detector for each different area. Only the measurements from those areas which are determined to have a sufficient amount of sample based on the amount of reflected light detected therefrom, i.e., are sufficiently wetted by sample, are used in the determination of analyte concentration, where the areas determined not to have sufficient sample, i.e., not to be sufficiently wetted by sample, are not used or rather are excluded from the determination of analyte concentration.

The subject invention is suitable for use with a variety of colorimetric, photometric or optical (herein used interchangeably) type test strips as are known in the art, where representative calorimetric test strips will be described in greater detail below. Such test strips find use in the determination of a wide variety of different analyte concentrations, where representative analytes include, but are not limited to, glucose, cholesterol, lactate, alcohol, bilirubin, hematocrit, and the like. In many embodiments, the test strips used with the subject invention are used to determine the glucose concentration in a physiological sample, e.g., interstitial fluid, blood, blood fractions, constituents thereof, and the like.

In further describing the subject invention, a review of representative colorimetric test strips that may find use with the subject apparatuses is provided first to provide a proper foundation for the subject invention, where such a review is by way of example and is not intended to limit the scope of the invention. The review of representative test strips is followed by a description of the subject apparatuses and the subject methods. Finally, a description of kits for use in practicing the subject methods is provided.

Representative Colorimetric Test Strips

Figure 1:
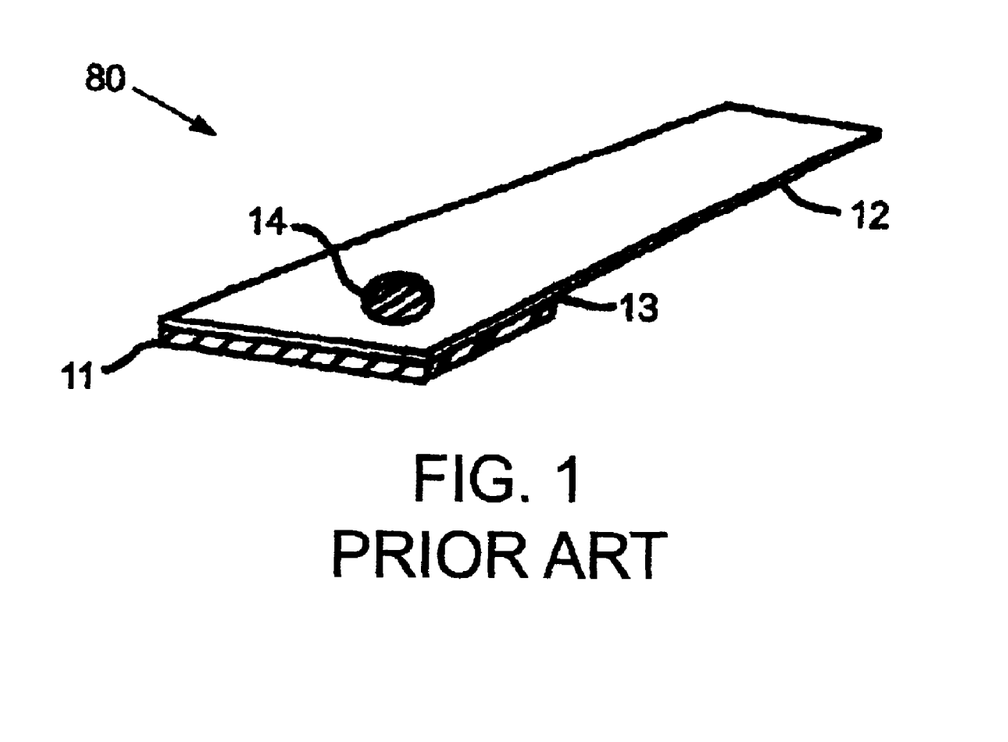
FIG. 1 an exemplary, representative colorimetric test strip suitable for use with the subject invention.

The colorimetric reagent test strips employed in these embodiments of the subject invention are generally made up of at least the following components: a matrix 11 for receiving a sample, a reagent composition (not shown as a structural component) that typically includes one or more members of an analyte oxidation signal producing system and a support element 12. The colorimetric test strips are configured and adapted to be received in an automated meter, as described below, for automatically determining the concentration of an analyte. An exemplary embodiment of a representative colorimetric test strip is shown in FIG. 1. FIG. 1 shows colorimetric test strip 80 in which matrix 11 is positioned at one end of support element 12 with adhesive 13. A hole 14 is present in support element 12 in the area of matrix 11 in which a sample can be applied to one side of matrix 11 and a reaction can be detected therefrom. Usually, sample is applied to one side of matrix 11 and a reaction is detected at another or opposite side of matrix 11, however, other configurations are possible as well. The components of a representative, exemplary colorimetric test strip will now be described in more detail.

Matrix

Matrix 11 is made of an inert material which provides a support for the various members of the signal producing system, described below, as well as the light absorbing or chromogenic product, i.e., the indicator, produced by the signal producing system. Matrix 11 is configured to provide a location for the physiological sample, e.g., blood, application and a location for the detection of the light-absorbing product produced by the indicator of the signal producing system. As such, the latter location may be characterized as the testing, detection or measurement area of the test strip. As such, matrix 11 is one that is permissive of aqueous fluid flow through it and provides sufficient void space for the chemical reactions of the signal producing system to take place. A number of different matrices have been developed for use in various analyte detection assays, which matrices may differ in terms of materials, dimensions and the like, where representative matrices include, but are not limited to, those described in U.S. Pat. Nos.: 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference. In principle, the nature of matrix 11 is not critical to the subject test strips and therefore is chosen with respect to other factors, including the nature of the instrument which is used to read the test strip, convenience and the like. As such, the dimensions and porosity of the matrix may vary greatly, where matrix 11 may or may not have pores and/or a porosity gradient, e.g. with larger pores near or at the sample application region and smaller pores at the detection region. The materials from which matrix 11 may be fabricated vary, and include polymers, e.g. polysulfone, polyamides, cellulose or absorbent paper, and the like, where the material may or may not be functionalized to provide for covalent or non-covalent attachment of the various members of the signal producing system.

Signal Producing System

In addition to matrix 11, the test strips further include one or more members of a signal producing system which produces a detectable product in response to the presence of analyte, which detectable product can be used to derive the amount of analyte present in the assayed sample. In the test strips, the one or more members of the signal producing system are associated, e.g., covalently or non-covalently attached to, at least a portion of (i.e., the detection, testing or measurement area) matrix 11, and in certain embodiments to substantially all of matrix 11.

In certain embodiments, e.g., where glucose is the analyte of interest, the signal producing system is an analyte oxidation signal producing system. By analyte oxidation signal producing system is meant that in generating the detectable signal from which the analyte concentration in the sample is derived, the analyte is oxidized by one or more suitable enzymes to produce an oxidized form of the analyte and a corresponding or proportional amount of hydrogen peroxide. The hydrogen peroxide is then employed, in turn, to generate the detectable product from one or more indicator compounds, where the amount of detectable product generated by the signal measuring system, i.e. the signal, is then related to the amount of analyte in the initial sample. As such, the analyte oxidation signal producing systems present in the subject test strips are also correctly characterized as hydrogen peroxide based signal producing systems.

As indicated above, the hydrogen peroxide based signal producing systems include a first enzyme that oxidizes the analyte and produces a corresponding amount of hydrogen peroxide, i.e., the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may also be employed. In those preferred embodiments where the reagent test strip is designed for the detection of glucose concentration, the first enzyme is glucose oxidase. The glucose oxidase may be obtained from any convenient source, e.g. a naturally occurring source such as *Aspergillus niger* or Penicillum, or recombinantly produced.

A second enzyme of the signal producing system may be an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Y. Ci, F. Wang; Analytica Chimica Acta, 233 (1990), 299–302.

The indicator compound or compounds, e.g., substrates, are ones that are either formed or decomposed by the hydrogen peroxide in the presence of the peroxidase to produce an indicator dye that absorbs light in a predetermined wavelength range. Preferably the indicator dye absorbs strongly at a wavelength different from that at which the sample or the testing reagent absorbs strongly. The oxidized form of the indicator may be a colored, faintly-colored, or colorless final product that evidences a change in color of the testing side of the membrane. That is to say, the testing reagent can indicate the presence of glucose in a sample by a colored area being bleached or, alternatively, by a colorless area developing color.

Indicator compounds that are useful in the present invention include both one- and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and 3-methyl-2-benzothiazolinonehydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments, signal producing systems that produce a fluorescent detectable product (or detectable non-fluorescent substance, e.g. in a fluorescent background) may be employed, such as those described in: Kiyoshi Zaitsu, Yosuke Ohkura: New fluorogenic substrates for Horseradish Peroxidase: rapid and sensitive assay for hydrogen peroxide and the Peroxidase. Analytical Biochemistry (1980) 109, 109–113.

Support Element

Matrix 11 is usually attached to a support element 12. Support element 12 may be of a material that is sufficiently rigid to be inserted into an automated device such as a meter without undue bending or kinking. Matrix 11 may be attached to support element 12 by any convenient mechanisms, e.g., clamps, adhesive, etc., herein shown attached using an adhesive 13. In many embodiments, support member 12 is made of material such as polyolefins, e.g., polyethylene or polypropylene, polystyrene or polyesters. Consequently, the length of the support element 12 typically dictates or corresponds to the length of the test strip. In the example shown in FIG. 1, one support element 12 is employed on one side of matrix 11. However, in certain embodiments, another support element is attached to the other side of matrix 11 so as to "sandwich" the matrix between two support elements.

Regardless of whether or not the length of support element 12 dictates or corresponds to the length of test strip 80, the total length of the test strip 80 generally ranges from about 20 mm to about 80 mm, usually from about 20 mm to about 65 mm and more usually from about 39 mm to about 57 mm, the width of the test strip 80 typically ranges from about 5 mm to about 25 mm, more usually from about 6 mm to about 19 mm and the thickness of the test strip 80 typically ranges from about 0.15 mm to about 0.40 mm, more usually from about 0.18 mm to about 0.38 mm.

As described above, support element 12 is usually configured to enable test strip 80 to be used with or inserted into a meter. As such, support element 12, and thus test strip 80, is typically in the form of a substantially rectangular or square-like strip, where the dimensions of support element 12 vary according to a variety of factors, as will be apparent to those of skill in the art.

In using such a colorimetric test strip, sample is allowed to react with the members of the signal producing system to produce a detectable product that is present in an amount proportional to the initial amount present in the sample. The amount of sample that is introduced to matrix 11 of the test strip may vary, but generally has a volume ranging from about 0.5 $\mu$l to about 10 $\mu$l. The sample may be introduced to matrix 11 using any convenient protocol, where the sample may be injected, allowed to wick, or be otherwise introduced. The amount of detectable product, i.e., signal produced by the signal producing system, is then determined and related to the amount of analyte in the initial sample. As mentioned above, in many embodiments sample is applied to one side or a first side of matrix 11 and the amount of detectable product is then determined at another or second side of matrix 11, where in many embodiments the amount of detectable product is determined on a side opposite the first side. In certain embodiments, automated meters that perform the above mentioned detection and relation steps are employed, as noted above. The above described reaction, detection and relating steps, as well as instruments for performing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

Examples of colorimetric reagent test strips that may be used with the subject invention include, but are not limited to, those described in U.S. Pat. Nos.: 5,049,487; 5,563,042; 5,753,452; 5,789,255, the disclosures of which are herein incorporated by reference.

The Optical Apparatuses

As summarized above, the subject invention provides apparatuses, i.e., optical meters, for use with test strips, such as the type described above, and which are configured to determine the concentration of at least one analyte in a physiological sample applied to the test strip. The optical meters of the subject invention include at lest one light source for illuminating a testing area of a test strip that is inserted into the meter, a detector array made-up of a plurality of detectors for detecting reflected light from each different area of the testing area of the test strip respectively, means for determining whether each different area of the testing area has a sufficient amount of sample based on the amount of reflected light detected therefrom, and means for determining, from only those areas determined to have a sufficient amount of sample, i.e., those areas determined to be sufficiently wetted by sample, the concentration of at least one analyte in the physiological sample applied to the test strip.

The size of the subject meters will vary depending on a variety of factors such as the size of the test strips used with the meters, the shape of the test strips, etc. However generally, the meters of the subject invention are small enough to be portable or easily moveable. By way of example, the length of an apparatus typically ranges from about 45 mm to about 160 mm and more usually from about 50 mm to about 150 mm, the width typically ranges from about 35 mm to about 80 mm and more usually from about 40 mm to about 75 mm and the thickness typically ranges from about 10 mm to about 30 mm and more usually from about 10 mm to about 25 mm.

Likewise, the shapes of the subject meters will vary, where the shapes may range from simple to complex. In many embodiments, the subject meters will assume a circular, oblong, oval, square or rectangular shape, although other shapes are possible as well, such as irregular or complex shapes.

The subject meters will now be further described with reference to the Figures, where like numerals represent like components or features. An exemplary embodiment of a subject apparatus 20 is shown schematically in FIG. 2 where a portion of representative test strip 80, i.e., matrix or testing area 11 affixed to a portion of support 12, is shown operatively associated with apparatus 20.

Figure 2:
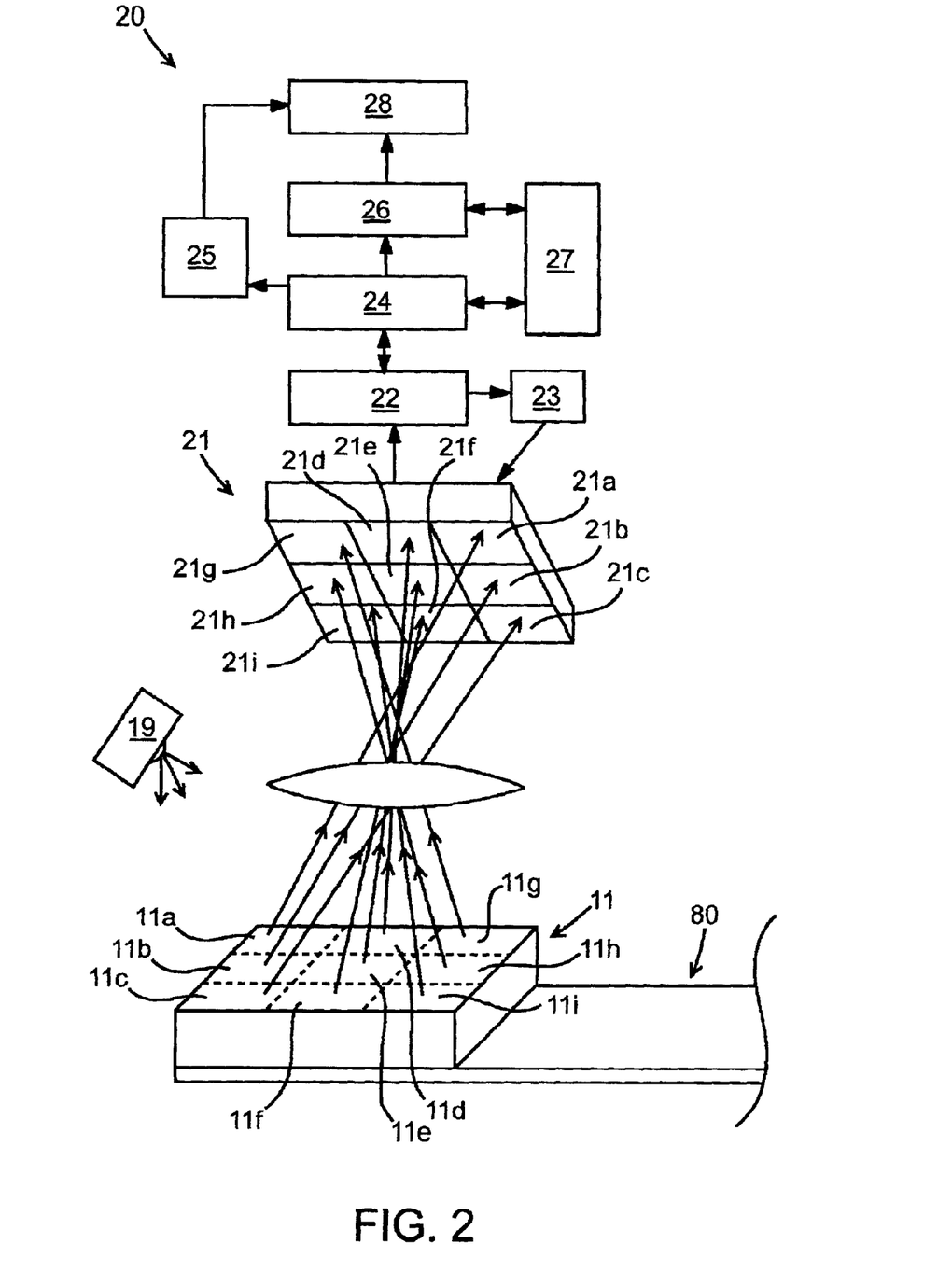
FIG. 2 is a schematic view of an exemplary embodiment of a subject apparatus having a test strip associated therewith.

As mentioned above, apparatus 20 includes at least one light source 19. Light source 19 projects light onto the area of the test strip, e.g., matrix 11, having sample applied thereto and which has reagents for reacting with certain analytes in the sample, as described above. More specifically, light source 19 projects light onto the testing area of matrix 11, i.e., all of the testing areas 11a–11N of matrix 11. Light source 19 typically includes a light emitting diode (LED) or any other convenient light source such as a laser diode, a filtered lamp, a phototransistor, and the like. Usually, light source 19 contains two or more LED sources, e.g., three LED sources, or a single diode capable of emitting two or more distinct wavelengths of light. Light source 19 is usually capable of emitting light at wavelengths ranging from about 400 nm to about 1000 nm, usually from about 500 nm to about 940 nm. For example, where two distinct wavelengths are employed, light source 19 is capable of emitting light at about 635 nm and about 700 nm and in many embodiments the light source is capable of emitting light at about 660 nm and 940 nm, and in certain embodiments the light source is capable of emitting light at about 525 nm, 630 nm and 940 nm. It will be apparent that the wavelengths described herein are for exemplary purposes only and are in no way intended to limit the scope of the invention as many other combinations of wavelengths are possible as well. Commercially available light sources that produce wavelengths of light described above are known in the art and include, but is not limited to, an LYS A676 light source capable of emitting light of 635 nm and 700 nm available from ASRAM Opto Semiconductor, Inc.

Apparatus 20 also includes a plurality of light detectors or rather an array of detectors 21. By plurality is meant greater than about two detectors. Typically, about three detectors or more are present, e.g., in a linear or triangular arrangement, usually about four detectors or more are present (e.g., configured in a 2×2 arrangement), where the number of detectors may range from about 6 detectors to about 100 or more detectors, where the number of detectors employed will vary depending on the size and shape of the testing area of matrix 11, etc. In other words, the number of individual detectors that make-up detector array 21 is related to the number of discrete sections or areas of a testing area that are measured. Of interest are detector arrays that include about 9 detectors, e.g., in a 3×3 arrangement, about 16 detectors, e.g., in a 4×4 arrangement, and about 25 detectors or more, e.g., in a 5×5 arrangement or in an 8×8 arrangement for embodiments having 64 detectors, etc., for example for use with rectangular or square-like shaped testing areas. In certain embodiments of the subject invention employing a charge coupled device ("CCD") camera array, the array may have about 1,000 or more detectors, e.g., arranged in a 512×494 arrangement or 1024×2048 arrangement. Accordingly, the number of detectors of the detector array may range from about 2 to thousands. By way of example only and not in any way intended to limit the scope of the invention, for a testing area that has a length ranging from about 2 mm to about 6 mm and a width ranging from about 2 mm to about 6 mm, the number of detectors will usually range from about 9 to about 100, and more usually from about 25 to about 64.

The configuration of the detectors that make up the detector array may vary according to a variety of factors such as the size and shape of the testing area and the like; however, the detector array is configured as a single unit. That is, the detectors are associated together to form one piece or one component, e.g., in a matrix or grid type arrangement or pattern or the like.

Figure 3A:
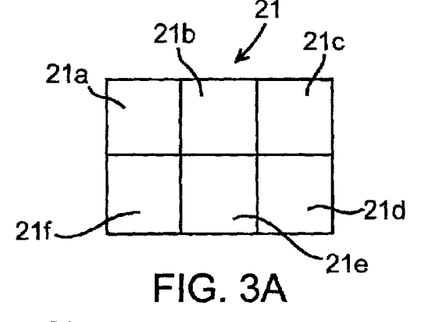
FIGS. 3A–3H show enlarged, plan views of various exemplary embodiments of the detector array of the subject invention having the individual detectors in a variety of configurations.
Figure 3B:
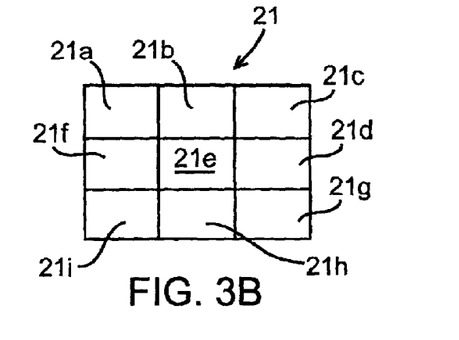
Figure 3C:
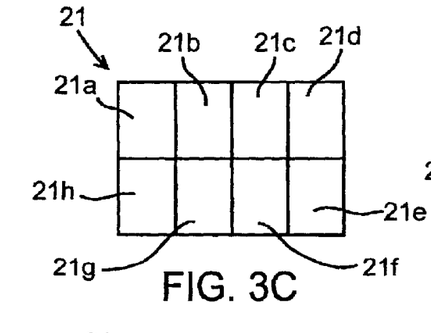
Figure 3D:
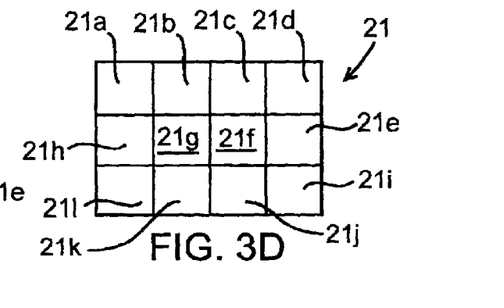
Figure 3E:
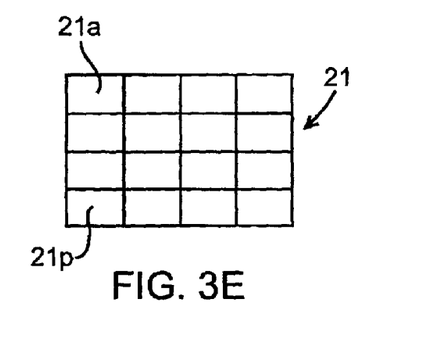
Figure 3F:
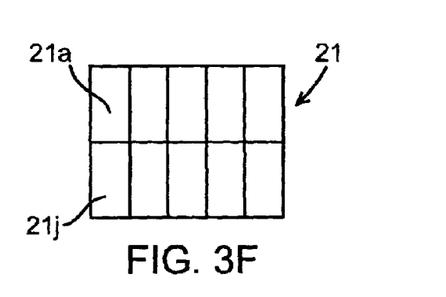
Figure 3G:
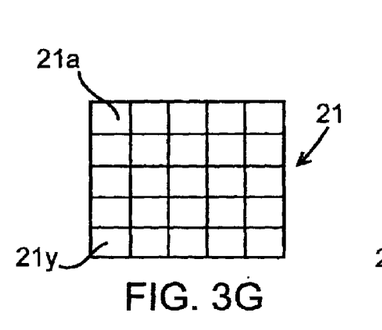
Figure 3H:
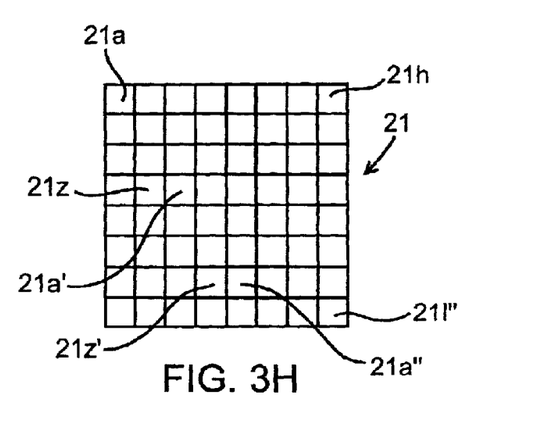

FIGS. 3A–3H show exemplary embodiments of the subject detector array having a number of different detectors 21a–21N in a variety of configurations, where such numbers of detectors and configurations thereof are exemplary only and are in no way intended to limit the scope of the invention. Accordingly, FIG. 3A shows an exemplary embodiment of detector array 21 having 6 detectors, first detector 21a, second detector 21b, third detector 21c, fourth detector 21d, fifth detector 21e and sixth detector 21f, configured in a 3×2 arrangement. FIG. 3B shows an exemplary embodiment of detector array 21 having 9 detectors, first detector 21a, second detector 21b, third detector 21c, fourth detector 21d, fifth detector 21e, sixth detector 21f, seventh detector 21g, eighth detector 21h and ninth detector 21i, configured in a 3×3 arrangement. FIG. 3C shows an exemplary embodiment of detector array 21 having 8 detectors, 21a–21h, configured in a 4×2 arrangement. FIG. 3D shows an exemplary embodiment of detector array 21 having 12 detectors, 21a–21l, configured in a 4×3 arrangement. FIG. 3E shows an exemplary embodiment of detector array 21 having 16 detectors, 21a–21p, configured in a 4×4 arrangement. FIG. 3F shows an exemplary embodiment of detector array 21 having 10 detectors, 21a–21y, configured in a 5×2 arrangement. FIG. 3G shows an exemplary embodiment of detector array 21 having 25 detectors, 21a–21y, configured in a 5×5 arrangement. FIG. 3H shows an exemplary embodiment of detector array 21 having 64 detectors 21a–21l" configured in an 8×8 arrangement. As is apparent, the number of individual detectors and the configuration thereof employed to make-up a subject detector array may vary as appropriate, e.g., may be made or less or more detectors than shown herein.

As described above, each detector of detector array 21 is capable of detecting or intercepting reflected light, e.g., diffusely reflected light, from a respective area or section of a testing area of matrix 11. That is, with respect to FIG. 2 for example, each detector 21a to 21i of detector array 21 detects reflected light from a corresponding, discrete, single respective area of matrix 11. As shown in FIG. 2, first detector 21a collects reflected light from first area 11a, second detector 21b detects light from second area 11b, third detector 21c detects light from third area 11c, fourth detector 21d detects light from fourth area 11d, fifth detector 21e detect light from fifth area 11e, sixth detector 21f detect light from fifth area 11f, seventh detector 21g detects light from seventh area 11g, eight detector 21h detects light from eight area 11h and ninth detector 21i detects light from ninth area 11i. The size of the discrete, corresponding area detected by each detector will vary depending on a variety of factors including, but not limited to, the number of detectors employed, the size of the matrix, etc. Signals from each detector are transmitted to one or more analysis means for analysis, as will be described in greater detail below, for determining whether each area has a sufficient amount of sample applied thereto.

Figure 4A:
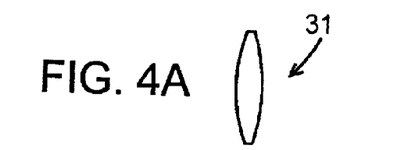
FIGS. 4A–4C show exemplary embodiments of imaging optics of the subject invention.
Figure 4B:
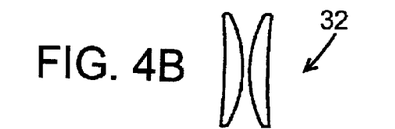
Figure 4C:
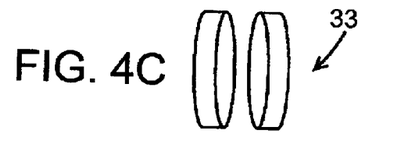

Apparatus 20 also includes imaging optics 31 for imaging reflected light from specific areas of matrix 11 onto specific, respective detectors. As shown in FIG. 2, imaging optics 31 is configured to image light from first area 11a onto first detector 21a, light from second area 11b onto second detector 21b, light from third area 11c onto third detector 21c and light from fourth area 11d onto fourth detector 21d, and so forth for each area and respective detector of the detector array as appropriate. Imaging optics 31 may take the form of one or more lenses or mirrors or combination thereof. For example, in certain embodiments, imaging optics 31 may take the form of a single element lens such as a double convex lens, as shown in FIG. 2 and FIG. 4A. In certain other embodiments, imaging optics may take the form of a double element lens such as two plano-convex lenses shown in FIG. 4B. In other embodiments, an achromat lens system whereby two achromatic lenses, each having convex crown surfaces, face each other, as shown in FIG. 4C, may be used. The lens configurations described above are known in the art.

Apparatus 20 also includes means 24 for determining whether a sufficient amount or volume of sample is present in each area that makes-up the testing area of matrix 11, where such determination is based upon the amount of reflected light detected from each area, i.e., from the area which each detector detects reflected light. This means is generally a digital integrated circuit 24, where such a digital integrated circuit 24 is under the control of a software program and thus is suitably programmed to execute all of the steps or functions required of it to determine whether reflected light detected from each area indicates a sufficient amount of sample, or any hardware or software combination that will perform such required functions. That is, sample amount determination means 24 is capable of executing or following an algorithm stored in the meter to determine, based on reflected light detected from each area of matrix 11, whether sufficient sample is present in each area. Sample amount determination means 24 usually reads the output of a signal conversion element such as analog/digital converter 22 which converts an analog signal from each detector to a digital signal. Accordingly, Sample amount determination means 24 is capable of carrying out all the steps necessary to determine whether reflected light detected from a particular area of the test strip indicates a sufficient amount of sample in that area, i.e., indicates that a particular area is sufficiently wetted with sample or not.

In addition to the above means for determining whether sufficient sample is present in each of the at least two areas on a test strip, the subject meters also include means 26 for determining the concentration of an analyte in the sample based on the areas determined to have a sufficient amount of sample based on the reflected light detected from those areas of the test strip, where areas determined not to have a sufficient amount of sample or are not satisfactorily wetted with sample are not used to determine analyte concentration. This means is generally a digital integrated circuit 26, where such a digital integrated circuit 26 is under the control of a software program and thus is suitably programmed to execute all of the steps or functions required of it, or any hardware or software combination that will perform such required functions. That is, analyte concentration determination means 26 is capable of executing or following an algorithm stored in the meter to determine analyte concentration from those areas determined to have sufficient sample, where the areas determined not to have sufficient sample are excluded from the determination of analyte concentration. (Analyte concentration determination means 26 is shown in FIG. 2 as a separate component from sample amount evaluation means 24, but in certain embodiments means for determining whether a sufficient amount of sample is present and means for determining the concentration of an analyte based on the those areas determined to have sufficient sample may be the same integrated circuit.) Accordingly, digital integrated circuit 26 is capable of carrying out all the steps necessary to exclude, from its determination of analyte concentration, any areas determined to have an insufficient sample based on the reflective light values detected therefrom and include only those areas of the test strip where sufficient sample is present, i.e., the sufficiently wetted areas.

The subject methods may also include means 23 for calibrating the apparatus and specifically each detector of the array detector independently. This means is generally a digital integrated circuit 23, where such a calibration means 23 is under the control of a software program and thus is suitably programmed to execute all of the steps or functions required of it, or any hardware or software combination that will perform such required functions. That is, calibration means 23 is capable of executing or following an algorithm stored in the meter for calibrating the meter, e.g., each detector of the detector array 21. (Calibration means 23 is shown in FIG. 2 as a separate component from sample amount determination means 24 and analyte concentration determination means 26, but in certain embodiments may be the same integrated circuit as one or both of means 24 and means 26.) Accordingly, calibration means 23 is capable of carrying out all the steps necessary to calibrate each detector of the apparatus independently.

The subject meters may also include means for determining the total volume of sample applied to a test strip 25, where such a total sample volume determination is based upon the amount of reflected light detected from each area determined to have a sufficient amount of sample. This means is generally a digital integrated circuit 25, where such a digital integrated circuit 25 is under the control of a software program and thus is suitably programmed to execute all of the steps or functions required of it to determine the total sample volume applied to the test strip, or any hardware or software combination that will perform such required functions. That is, total sample volume means 25 is capable of executing or following an algorithm stored in the meter to determine, based on reflected light detected from each area of the test strip determined to have a sufficient amount of sample, the total sample volume applied to the test strip.

The subject meters also include program and data memory 27, which may be a digital integrated circuit, that stores data and the operating program of one or more of the digital integrated circuits of the meter. The subject meters also include reporting device 28 for communicating total sample volume, results of analyte concentration, error messages, etc., to the user. Accordingly, reporting device 28 may take various hard copy and soft copy forms. Usually it is a visual display such as a liquid crystal display (LCD) or light emitting diode (LED) display, but it may also be a tape printer, audible signal, or the like.

Methods

The subject invention also provides methods for determining the concentration of an analyte in a physiological sample applied to a test strip. Specifically, the subject invention provides methods for determining the concentration of an analyte in a physiological sample applied to a test strip even in those instances where the entire area of the test strip where measurements are taken, i.e., the testing area, detection area or measurement area, is not entirely wetted by the sample either because too small of an amount of sample is applied thereto to wet the entire area and/or sample is applied unevenly or nonuniformly.

As such, it will be apparent that the subject methods provide the accurate determination of one or more analyte concentrations using small sample amounts, i.e., sample amounts less than conventionally required. In current practice, sample amounts of about 5 $\mu$l or more are needed to wet a testing area of a test strip for accurate analyte concentration determination. However, because the entire testing area need not be wetted in order to obtain accurate analyte concentration determinations using the subject methods, sample amounts less than about 5 $\mu$l, oftentimes less than about 3 $\mu$l may be used, where sample amounts of about 2 $\mu$l or less may be used in the subject methods in certain embodiments. For example, in certain embodiments sample volumes of about 0.5 $\mu$l may be used to obtain an accurate analyte concentration determination. Sample may be introduced into the appropriate area of the test strip using any convenient protocol, where sample may be injected, wicked, etc., as may be convenient. Sample may be applied to a test strip before or after the test strip is inserted into or otherwise operatively associated with a subject apparatus such that the testing area, i.e., each area of the testing area, of the test strip may register with the optical components of the apparatus.

Generally, the subject methods include applying sample to a testing area of a test strip, illuminating the testing area with light, obtaining a reflectance value from different areas of the testing area separately or independently, determining whether the obtained reflectance value from each area indicates that a sufficient amount of sample is present in each of the areas, i.e., determining whether each area is sufficiently wetted by sample, and deriving the concentration of at least one analyte from the areas determined to have a sufficient amount of sample, where the areas determined not to have a sufficient amount of sample are not used in analyte concentration determination, i.e., non-wetted or insufficiently wetted areas are excluded from the analyte concentration determination computations. Methods for generally deriving analyte concentration from reflectance values are known in the art, for example see U.S. Pat. No. 5,059,394, the disclosure of which is herein incorporated by reference.

A feature of the subject methods is that instead of deriving a single reflectance value for the entire testing area as is commonly done, multiple reflectance values are derived from multiple, discrete areas of the testing area. In this way, those areas of the testing area having insufficient sample may be identified and omitted from analyte concentration determination.

Accordingly, each detector of an array of detectors, i.e., of a plurality of detectors, detects reflected light from a discrete, respective section or area of a test strip, i.e., from a specific number or areas of the test strip, respectively, where imaging optics may be employed to focus or direct the light from specific areas onto specific detectors. By plurality is meant greater than about two detectors. Typically, about three detectors or more detect light from the test strip, usually about four detectors or more detect light from the test strip, where as many as about 6 detectors to about 100 or more detect light from the test strip in certain embodiments, where in some embodiments 1000 detectors or more detect light from the test strip, where the number of detectors employed will vary depending on the size and shape of the testing area of the test strip, etc. The detectors of the detector array may detect the light at substantially the same or different times, but typically the light from each area is detected at substantially the same time.

As mentioned above, reflectance values from discrete, independent areas of the test strip are detected by each corresponding detector. By reflectance value is meant any value or series of values, signals, or any data set, etc., relating to an observed amount of reflected light from a corresponding, respective area of the test strip. A reflectance value may be in any form, i.e., the reflectance value may be in raw or processed form. A reflectance value may be obtained periodically or substantially continuously over a period of time.

According to the subject methods, the observed, reflected light from each detector is determined to be indicative of a sufficient amount of sample or indicate that the area is sufficiently wetted by sample and, if indicative of such a sufficient amount of sample, is used to determine the concentration of analyte in the sample. In other words, a reflectance value from each detector is evaluated to determine if the corresponding area has sufficient sample volume or is sufficiently wetted by sample or wetted by enough sample to provide an accurate analyte concentration measurement, where the sample amount or volume in each area corresponds or is related to the light reflected therefrom, i.e., a reflectance value. Accordingly, the amount of sample required to be determined sufficient will vary depending on the analyte of interest, the size of each discrete or different area, etc. In many embodiments, an area will be determined to have sufficient sample if the surface area thereof is at least about 95 to about 100% covered with sample, usually at least about 98–100% covered with sample. It will be apparent to those of skill in the art that the reflectance value indicating or relating to such sufficient amount of sample will vary depending on a variety of factors including, but not limited to, the type of sample, the analyte of interest, etc. Sufficient sample amounts of an area may be determined in any convenient manner, where the following embodiments are provided by way of example and are in no way intended to limit the scope of the invention. In all embodiments, a reflectance value is determined for each detector of the detector array, as described above, where the determined reflectance value is related to the amount, if any, of sample or wetting of a corresponding area.

Figure 5:
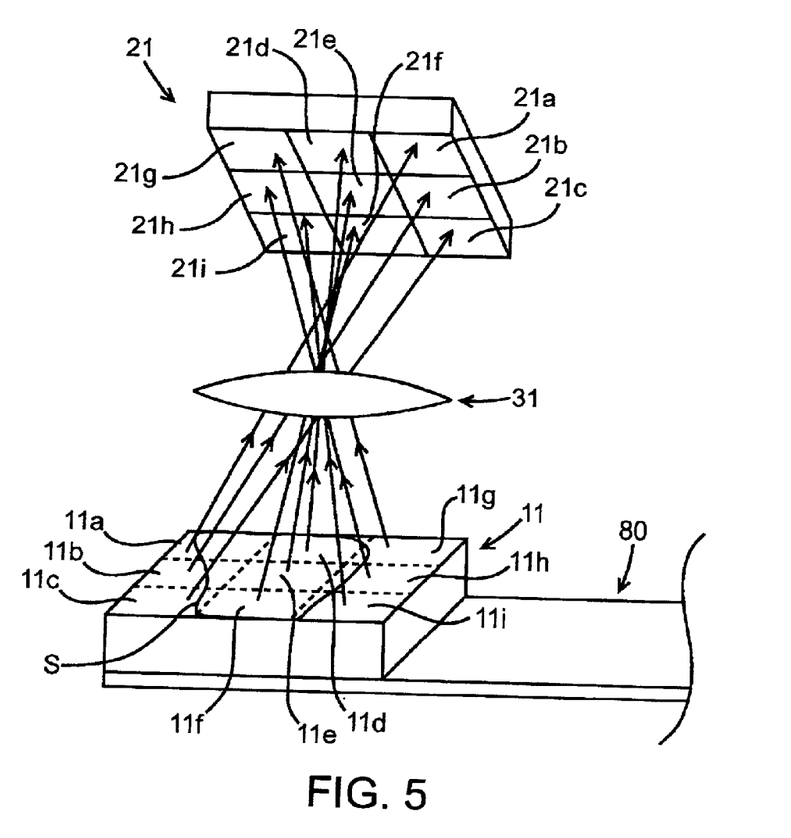
FIG. 5 shows an exemplary embodiment of an exemplary measurement area of a test strip with a detector array of the subject invention.

In one embodiment, after a reflectance value is determined for each detector, the minimum reflectance value from amongst all the reflectance values is determined. Each reflectance value is then compared to this minimum value, whereby a reflectance value and corresponding area is determined to have a sufficient amount of sample if the reflectance value produced therefrom lies within a certain range of, i.e., is substantially the same as, the minimum reflectance value or of the area is the area that produces the minimum reflectance value. For example, if an area provides a reflectance value that is within about 5–10% of the minimum reflectance value, it is determined to have a sufficient amount of sample, i.e., it is substantially the same as to the minimum value, where the areas having reflectance values greater than about 5–10% of the minimum reflectance value are determined to have an insufficient amount of sample, i.e., are not substantially the same as the minimum value. For example, FIG. 5 shows matrix 11 operatively associated with detector 21 having detectors 21a–21i. Employing the method described above, the reflectance values from areas 11e and 11f would provide the minimum reflectance values as they are completely wetted by sample and are determined to have a sufficient amount of sample. Accordingly, the reflectance values from areas 11a, 11b, 11c, 11d, 11g, 11h and 11i are compared to the minimum reflectance value and any of the areas found to be with a certain range of the minimum reflectance value, e.g., within about 5–10% of the minimum reflectance value, are determined have sufficient sample, i.e., determined to be sufficiently wetted.

In another embodiment, a particular area is determined to have a sufficient amount of sample if it demonstrates a certain drop in reflectance, i.e., a predetermined drop in reflectance or greater, from a time prior to sample application to a time after sample application and each adjacent area produces at least some drop in reflectance beyond a certain minimum drop in reflectance. For example, referring again to FIG. 5, area 11f would produce a large change in reflectance from a time prior to sample application to a time after sample application because it is completely covered with sample. Furthermore, adjacent areas 11b, 11c, 11e, 11h and 11i all would produce at least some change in reflectance after sample application because all have at least some amount of sample. Accordingly, area 11f would be determined to have a sufficient amount of sample because it produced a drop in reflectance value that is equal to or greater than a predetermined drop in reflectance and each adjacent area produces at least some drop in reflectance. However, area 11c would be determined not to have a sufficient amount of sample because it would not produce a sufficient drop in reflectance.

In certain embodiments, an area is determined to have a sufficient amount of sample if it produces a certain reflectance value, e.g., is substantially the same as a predetermined reflectance value such as within about 5 to about 10% of a predetermined reflectance value, and meets any one, usually all, of the above-described criteria, i.e., (1) is an area that provides the minimum reflectance value from amongst all the areas, (2) produces a reflectance value that is within a certain range of the minimum reflectance value, or (3) produces a drop in reflectance that is as great or greater than a certain drop in reflectance and all adjacent areas also produce a certain minimum drop in reflectance. Such a method is particularly well suited for those areas that define the edges of the testing area.

As described above, once all the areas of the testing area are determined to have a sufficient amount of sample or not, i.e., the signal or reflectance from the detectors are determined to be sufficient or insufficient, the concentration of at least one analyte in the sample is determined, using the signals from only those areas having a sufficient amount of sample, where the concentration is related to the amount of light reflected from those areas having a sufficient amount of sample, as is known in the art. For example, reflectance values from the areas having a sufficient amount of sample may be compared to a standard curve or graph of analyte concentration versus reflectance and the analyte concentration in the sample of interest obtained therefrom (see for example U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference).

The above described reflectance values may be obtained using any convenient protocol, where the following protocol is offered by way of example and is in no way intended t limit the scope of the invention.

In many embodiments of the subject methods, each detector of the detector array is independently calibrated. Each detector may be calibrated using any convenient protocol. In one such protocol for calibrating each detector independently, each detector detects a "background" signal ($R_b$), which is performed before a test strip is inserted into the meter, e.g., before inserting a test strip at the time of testing or at the point of manufacture of the meter; regardless; it is performed before a test strip is associated with the meter. Once $R_b$ is measured for each detector, each detector detects a "dry" signal ($R_{dry}$). Usually, this is done with an unreacted test strip inserted into the meter, but before an application of sample thereto.

Once each detector has been calibrated, sample is applied to the test strip and the area is illuminated with light, usually with light of one or more wavelengths. In many embodiments, sample is applied to one side of the matrix and light illuminates and is detected from another side of the matrix referred to as the measurement or testing area of the test strip, e.g., the side opposite the sample application side. As described above, the presence or amount of reflectance is a result of formation of a reaction product when sample is applied to an area on the test strip having one or more signal producing components. In other words, the components of the signal producing system react to give a light absorbing reaction product.

The raw data described above are used to calculate parameters proportional to glucose concentration (see for example U.S. Pat. Nos. 5,059,394 and 5,304,468). A logarithmic transformation of reflectance analogous to the relationship between absorbance and analyte concentration observed in transmission spectroscopy can be used if desired. A simplification of the Kubelka-Monk reflectance equations, as known in the art, is of particular interest. Generally, the parameter K/S is used, where K is related to absorbance and S is related to scattering. In this derivation, K/S is related to analyte concentration, where K/S defined by Equation 1 as follows:

$$K/S_{-t} = (1-Rt)^2/2Rt \qquad \text{(Equation 1)}$$

Accordingly, Rt is the reflectivity taken at a particular time t described by Equation 2, where Rt is the reflectance, e.g., $R_{20}$ or $R_{30}$, etc., corresponding to 20 seconds, 30 seconds, etc. That is, each detector provides a reflectivity or an Rt value that corresponds to the signal measured from a corresponding area of the test strip matrix, where Rt varies from 0 for no reflected light ($R_b$) to 1 for total reflected light ($R_{dry}$).

$$Rt = (R_w - R_b)/(R_{dry} - R_b) \quad \text{(Equation 2)}$$

$R_w$ is the reflectance detected from an area by a detector.

Accordingly, K/S is derived for each detector and corresponding area of the testing area detected by a respective detector. As K/S is related to analyte concentration, a final or overall K/S value is determined using only those signals from detectors exhibiting a certain K/S value indicating an area having sufficient sample amount or sample wetting, where the overall K/S value is related to the concentration of analyte in the sample applied to the test strip.

The subject methods also include, in certain embodiments, the determination of the size of the sample applied to the matrix of a test strip, i.e., the total sample volume applied to the test strip. In this way, a user may be notified or alerted that sufficient sample has been applied or insufficient sample has been applied and more sample is required. Sample size is determined by computing the number of detectors that detect reflected light from areas determined to have a sufficient amount of sample, where the volume of sample accommodated by each area is known such that the total volume of sample applied to the test strip is determined by computing the number of areas having a sufficient amount of sample and the volume of sample retained in each area. Sufficiency of sample size may vary according to the particular analyte concentration(s) to be determined, etc., however usually sample amounts less than about 5 $\mu$l and oftentimes less than about 3 $\mu$l are sufficient, where sample amounts of about 2 $\mu$l or less, in many embodiments about 0.5 $\mu$l may be sufficient in certain embodiments.

The subject methods also include calibrating other components, features or aspects of the meter, such as calibrating the at least one light source, the detector array, the imaging optics, etc. (see for example copending U.S. application entitled "Devices and Methods for Analyte Concentration Determination" to Eyster and Wallace, filed on May 1, 2002, and copending U.S. application entitled "Devices and Methods for Analyte Concentration Determination" to Eyster and Wallace, filed on May 1, 2002, the disclosures of which are herein incorporated by reference.

Kits

Finally, kits for practicing the subject methods are provided. The subject kits include an apparatus according to the subject invention, i.e., a subject optical meter. The subject kits may also include one or more test strips, usually a plurality of test strips, such as the type of test strip described above. The subject kits may further include an element for obtaining a physiological sample. For example, where the physiological sample is blood, the subject kits may further include an element for obtaining a blood sample, such as a lance for sticking a finger, a lance actuation means, and the like. In addition, the subject kits may include a control solution or standard, e.g., a control solution that has a known analyte concentration such as a known glucose concentration. The kits may further include instructions for using the apparatus for determining the presence and/or concentration of at least one analyte in a physiological sample applied to a test strip. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides devices and methods for accurate analyte concentration determination in the cases where small sample volumes are applied to a test strip testing area and/or the testing area of the test strip is not evenly or uniformly wetted by sample. The above described invention provides a number of advantages, including, but not limited to, ease of use, portability, and accurate analyte concentration determinations using small amounts of sample, thereby reducing the likelihood of multiple finger sticks. As such, the subject invention represents a significant contribution to the art.

The subject invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

The specific devices and methods disclosed are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. An apparatus configured for receiving a test strip and for determining the concentration of at least one analyte in a physiological sample applied to the test strip, said apparatus comprising:

(a) at least one light source for irradiating a plurality of different areas of said test strip that has been operatively associated with said apparatus;

(b) a detector array for detecting reflected light from each of said plurality of different areas, respectively;

(c) means for determining whether each area of said plurality of different areas has a sufficient amount or sample based on said detected reflected light from each respective area; and (d) means for determining the concentration of at least one analyte based on said reflected light detected from those areas determined to have a sufficient amount of sample, wherein areas determined not to have a sufficient amount of sample are not used in said analyte concentration determination.

2. The apparatus according to claim 1, wherein said at least one light source is capable of emitting light in the wavelength from about 400 nm to about 1000 nm.

3. The apparatus according to claim 2, wherein said light source is capable of emitting light of at least two different wavelengths.

4. The apparatus according to claim 3, wherein a first wavelength of light is about 660 nm and a second wavelength of light is about 940 nm.

5. The apparatus according to claim 1, wherein from about 4 to about 1,000 detectors comprise said detector array.

6. The apparatus according to claim 1, wherein about 1,000 detectors or more comprise said detector array.

7. The apparatus according to claim 1, further comprising imaging optics for imaging reflected light from said plurality of areas onto respective detectors of said detector array.

8. The apparatus according to claim 1, further comprising means for calibrating said apparatus.

9. The apparatus according to claim 1, further comprising means for determining the total volume of sample applied to said test strip.

10. A kit for determining the concentration of an analyte in a physiological sample, said kit comprising:

(a) an apparatus according to claim 1; and (b) instruction for using said apparatus for determining the concentration of at least one analyte in a physiological sample.

11. The kit according to claim 10, further comprising at least one test strip.

12. The kit according to claim 10, further comprising at least one of an element for obtaining sample and control solution.

13. A method for determining the concentration of at least one analyte in a physiological sample applied to a test strip, said method comprising:
  (a) illuminating a plurality of different areas of said test strip having physiological sample applied thereto;
  (b) obtaining a respective reflectance value from each area of said plurality of different areas;
  (c) determining whether each area of said plurality of different areas has a sufficient amount of sample based on said obtained respective reflectance value;
  (d) deriving the concentration of said at least one analyte in said physiological sample from each of said plurality of different areas determined to have a sufficient amount of sample, wherein areas determined not to have a sufficient amount of sample are not used in said derivation.

14. The method according to claim 13, wherein said step of determining comprises determining the minimum reflectance value from amongst each of said obtained reflectance values and comparing each of said obtained reflectance values to said minimum reflectance value, whereby an area is determined to have a sufficient amount of sample if it produces said minimum reflectance value or produces a reflectance value that is substantially the same as said minimum reflectance value.

15. The method according to claim 13, wherein said step of determining comprises determining a drop in reflectance for each of said plurality of areas from a time prior to sample application to a time after sample application and comparing said drop in reflectance to a predetermined drop in reflectance value, whereby an area is determined to have a sufficient amount of sample if is produces a drop in reflectance equal to or greater than said predetermined drop in reflectance value.

16. The method according to claim 15, further comprising determining if all areas adjacent an area determined to have said drop in reflectance equal to or greater than said predetermined drop in reflectance value also have a minimum drop in reflectance.

17. The method according to claim 13, wherein said step of determining comprises determining whether each of said obtained reflectance values is substantially the same as a predetermined reflectance value and at least one of: (a) determining the minimum reflectance value from amongst each of said obtained reflectance values and comparing each of said obtained reflectance values to said minimum reflectance value, (b) determining a drop in reflectance from a time prior to sample application to a time after sample application and comparing said drop in reflectance to a predetermined drop in reflectance value, and (c) determining if all areas adjacent an area determined to have said drop in reflectance equal to or greater than said predetermined drop in reflectance value also have a minimum drop in reflectance.

18. The method according to claim 13, wherein said step of obtaining comprises providing a detector array comprised of a plurality of detectors, wherein each detector of said detector array obtains said reflectance value from a respective area of said test strip.

19. The method according to claim 18, further comprising calibrating each of said detectors separately.

20. The method according to claim 13, further comprising determining the total volume of sample applied to said test strip.

21. The method according to claim 20, wherein said step of determining total sample volume comprises computing the number of areas on the test strip determined to have a sufficient amount of sample.

22. The method according to claim 13, wherein said physiological sample is blood.

* * * * *